(12) United States Patent
Nishimoto

(10) Patent No.: US 6,534,778 B1
(45) Date of Patent: Mar. 18, 2003

(54) APPARATUS FOR DETECTING BALLS CARRIED IN TUBE

(75) Inventor: Ikuo Nishimoto, Tokyo (JP)

(73) Assignee: Yamatake Corporation, Tokyo (JP)

( * ) Notice: Subject to any disclaimer, the term of this patent is extended or adjusted under 35 U.S.C. 154(b) by 73 days.

(21) Appl. No.: 09/617,210

(22) Filed: Jul. 17, 2000

(30) Foreign Application Priority Data

May 24, 2000 (JP) ........................................ 2000-153138

(51) Int. Cl.[7] ................................................ G01N 21/85
(52) U.S. Cl. .................................. 250/574; 250/222.1
(58) Field of Search ................................... 250/573, 574, 250/576, 222.2, 222.1, 559.11, 559.12; 73/53.01, 61.69, 61.48; 340/627; 356/441, 442

(56) References Cited

U.S. PATENT DOCUMENTS

| | | | | |
|---|---|---|---|---|
| 3,635,678 A | * | 1/1972 | Seitz et al. | 436/69 |
| 4,373,931 A | * | 2/1983 | Takekawa | 436/539 |
| 5,955,776 A | * | 9/1999 | Ishikawa | 257/618 |
| 6,043,871 A | * | 3/2000 | Solen et al. | 356/39 |
| 6,106,739 A | * | 8/2000 | Stephens et al. | 252/62.3 R |

* cited by examiner

Primary Examiner—Robert H. Kim
Assistant Examiner—Glen Kao
(74) Attorney, Agent, or Firm—Frishauf, Holtz, Goodman & Chick, P.C.

(57) ABSTRACT

A ball detecting apparatus having a simple structure and being capable of surely detecting balls carried in a tube using transparent liquid as a carrier without being affected by bubbles produced in the tube. The ball detecting apparatus has a surface light source 12 for projecting diffused light having a predetermined beam cross section and a predetermined beam spread angle, from a side of a tube 11 in which balls 10 are carried, into the tube 11. A photo detector 13 is arranged opposite to the surface light source 12 with the tube between. The photo detector receives a component of the diffused light that travels directly toward a light receiving area and/or a component of the diffused light that has been deflected by a bubble produced in the transparent liquid to travel toward the receiving area. The light receiving area is adapted to be able to be completely shielded from the diffused light by the balls. Judging means judges the presence of the balls in the tube based on a light receiving signal sent from the photo detector.

6 Claims, 3 Drawing Sheets

APPARATUS FOR DETECTING BALLS CARRIED IN TUBE

BACKGROUND OF THE INVENTION

1. Field of the Invention

The present invention relates to a ball detecting apparatus which can surely detect balls, for example, ball-shaped semiconductor devices provided with integrated function elements, when the balls are carried one by one in a transparent tube using transparent liquid as a carrier, for example, in the process of manufacturing the ball-shaped semiconductor devices.

2. Description of the Prior Art

These days, a ball semiconductor device is attracting attention. The ball semiconductor device is a ball-shaped semiconductor device of 1 mm or so in diameter provided with monolithicly integrated function elements such as a transistor and the like. It has been also proposed to construct a semiconductor circuit/system having a predetermined circuit function by combining a plurality of kinds of ball semiconductor devices each having a function of a basic element such as a sensor or a memory.

In the process of manufacturing ball semiconductor devices of that kind, balls that are ball semiconductor devices are carried one by one using transparent liquid like water as a carrier, in a ball carrying passage formed, for example, out of a transparent tube. Here, in controlling the manufacturing process, it is important to count the number of balls that have been carried, for example, in the tube. Conventionally, with a photo sensor that comprises a light source and a photo detector arranged opposite to each other with the tube between and has an optical path crossing the tube, balls passing the optical path are detected, making use of the fact that balls carried in the tube intercept the light.

However, sometimes, bubbles are produced in the transparent liquid as a carrier, and cause errors in detecting the balls.

Specifically, as schematically shown in FIG. 7, in a conventional ball detecting apparatus, an optical fiber 3 for projection is arranged on one side of the transparent tube 1 that forms a ball carrying passage to guide the light emitted from the light source 2 and project it to the transparent tube 1. Further, an optical fiber 4 for reception is arranged on the opposite side of the transparent tube 1 to guide the light having crossed the tube 1 to the photo detector 5. As shown in FIG. 8, when a ball 7 carried in the tube 1 by the transparent liquid 6 as a carrier intercepts the light crossing the tube 1, the photo detector 5 ceases to receive light. By making use of this, the ball 1 is detected.

However, sometimes, bubbles 8 are produced in the transparent liquid 6. The bubbles 8 can act as concave lenses. Therefore, sometimes, the light projected to the tube 1 is deflected as shown in FIG. 9 and cannot reach the optical fiber 4 for reception. As a result, the photo detector 5 ceases to receive the light from the light source 2, and the bubbles 8 are mistakenly detected as a ball 7. This may put the control of manufacturing process out of order. Thus, various conventional attempts are all devoted to preventing bubbles 8 being produced in the transparent liquid.

SUMMARY OF THE INVENTION

An object of the present invention is to provide a highly practical ball detecting apparatus having a simple structure and being capable of surely detecting balls carried in a tube without being affected by bubbles produced in transparent liquid.

The present invention provides technique for surely detecting non-transparent balls carried one by one in a transparent tube as a ball carrying passage using transparent liquid as a carrier, optically with an optical sensor comprising a light source and a photo detector.

The ball detecting apparatus of the present invention especially uses, as the light source of the optical sensor, a surface light source that projects diffused light having a predetermined beam cross section and a predetermined beam spread angle, from a side of the tube into the tube. The photo detector is arranged such that a light receiving area of the photo detector is opposite to the surface light source with the tube between. The photo detector receives a component of the diffused light that has passed through the transparent liquid toward the light receiving area, and/or a component of the diffused light that has been deflected by a bubble produced in the transparent liquid and come out of the transparent liquid toward the light receiving area. The light receiving area is adapted to be able to be completely shielded from the diffused light by the balls carried in the tube. Judging means is provided to judge the presence of the balls carried in the tube from the level of a light receiving signal sent from the photo detector.

Specifically, the ball detecting apparatus according to the present invention uses diffused light having a predetermined beam cross section and a predetermined beam spread angle as light for use in detecting balls, and uses a photo detector whose light receiving area is of dimensions such that it can be completely shielded from the diffused light by the balls carried in the tube, momentarily. Thus, the photo detector detects a component of the diffused light that has passed through the transparent liquid directly toward the light receiving area, and/or a component of the diffused light that has been deflected by a bubble produced in the transparent liquid to travel indirectly toward the light receiving area.

In a desirable embodiment of the present invention, the photo detector has a predetermined angular aperture, and a field of view determined by the angular aperture and the light receiving area is optically located such that the light receiving area can be completely shielded from the diffused light by the balls.

In a desirable embodiment of the present invention, the surface light source is arranged opposite to one side of the tube with an optical fiber between, and the photo detector is arranged opposite to the opposite side of the tube with an optical fiber between. The surface light source may include a light diffusing plate to produce the diffused light.

The balls may be, for example, ball-shaped semiconductor devices provided with or to be provided with an integrated circuit of function elements. Thus, the ball detecting apparatus according to the present invention is suitable to be used in the process of manufacturing such ball-shaped semiconductor devices.

With the ball detecting apparatus according to the present invention, in optically detecting balls carried in a tube using transparent liquid as a carrier, balls can be surely detected excluding the influence of bubbles in the transparent liquid easily and surely. Thus, the number of balls carried in the tube can be counted correctly, which, for example, makes the control of process of manufacturing ball semiconductor devices reliable and sure. In addition, the ball detecting apparatus according to the present invention has a simple structure, therefore it has a great practical effect such that the ball detecting apparatus operating with high reliability can be manufactured at low costs.

DETAILED DESCRIPTION OF THE INVENTION

Figure 1:
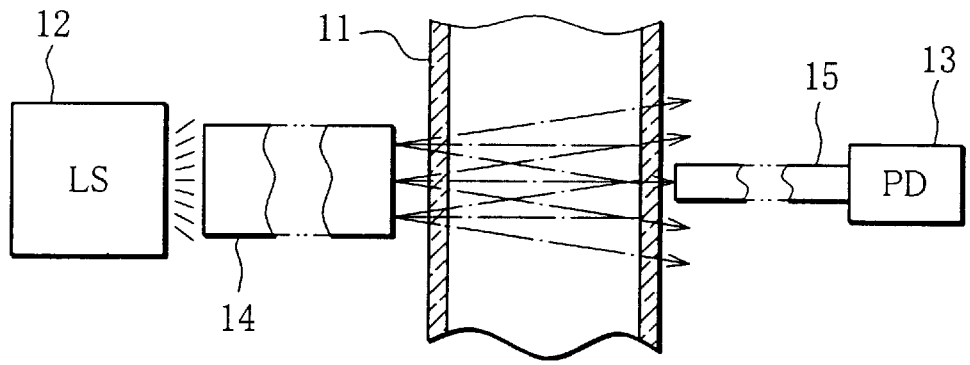
FIG. 1 is a diagram showing a schematic structure and optical system of a ball detecting apparatus for detecting balls carried in a tube according to an embodiment of the present invention.

Referring to the drawings, a ball detecting apparatus for detecting balls carried in a tube according to an embodiment of the present invention will be described below based on an example where an optically non-transparent ball 10 that is a ball-shaped semiconductor device is to be detected optically.

FIG. 1 is a diagram showing a schematic structure of a ball detecting apparatus according to an embodiment of the present invention. Reference numeral 11 denotes a transparent tube that forms a ball carrying passage. When to-be-detected balls 10 are 1 mm or so in diameter, a flexible tube of 1.2 mm or so in inner diameter is used for the tube 11. In the tube 11 is made to flow transparent liquid such as water, which serves as a carrier to carry the balls 10.

An optical sensor for detecting the balls 10 carried in the tube 11 in the above-described manner comprises a surface light source 12 and a photo detector 13. The surface light source 12 projects, to the tube 11, diffused light having a predetermined beam cross section and predetermined beam spread angle. The photo detector 13 is arranged opposite to the surface light source 12 with the tube 11 between, and receives the diffused light having crossed the tube 11. In the present embodiment, diffused light emitted from the surface light source 12 is guided by an optical fiber 14 for projection to a side of the tube 11 and projected to the tube 11. The photo detector 13 receives the diffused light emitted from the surface light source 12 through an optical fiber 15 for reception that is arranged opposite to the optical fiber 14 for projection in a coaxial manner.

Figure 2:
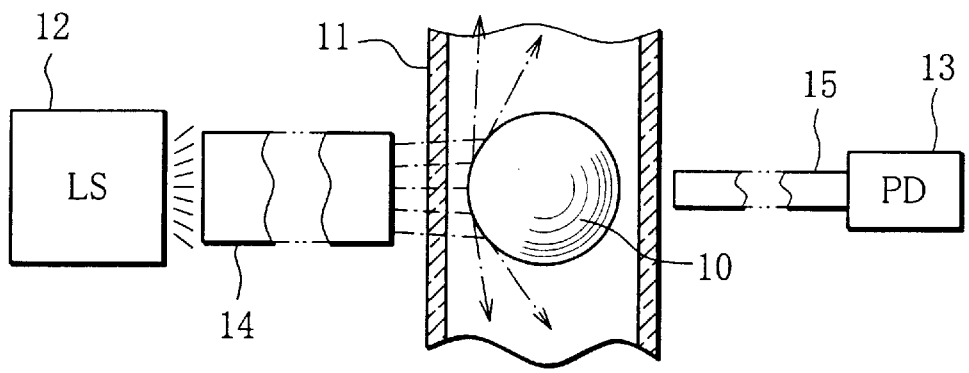
FIG. 2 is a diagram showing how a ball guided in a tube is sensed in the ball detecting apparatus of FIG. 1.

Particularly in the present embodiment, a large-diameter optical fiber is used for the optical fiber 14 for projection so that the diffused light emitted from the surface light source 12 having a predetermined beam cross section may be projected to the tube 11 maintaining that beam cross section. On the other hand, for the optical fiber 15 for reception is used an optical fiber whose light receiving area, which is determined by the diameter of an opening end face of the optical fiber and the light receiving angle (field of view angle) of the optical fiber, can be completely shielded from the diffused light by a ball 10 as shown in FIG. 2. Thus, generally, an optical fiber having a diameter smaller than that of the optical fiber 14 for projection is used for the optical fiber 15 for reception.

The photo detector 13, whose light receiving surface is opposite to the surface light source 12 with the optical fiber 14 for projection, tube 11 and optical fiber 15 for reception arranged in this order between, receives the light having reached its light receiving area, that is, the light receiving area of the optical fiber 15 for reception, and sends out an electric signal at a level corresponding to the amount of the received light. Normally, as shown in FIG. 1, the photo detector 13 receives, of the diffused light projected from the surface light source 12 to the tube 11, a component that has traveled straight through the transparent liquid. When a ball 10 carried in the tube 10 reaches a point opposite to the light receiving area of the photo detector 13 as shown in FIG. 2, the light receiving area of the photo detector 13 is completely shielded from the diffused light by the ball 10. Therefore, the photo detector 13 cannot receive the diffused light projected from the surface light source 12 to the tube 11, at all.

Figure 3:
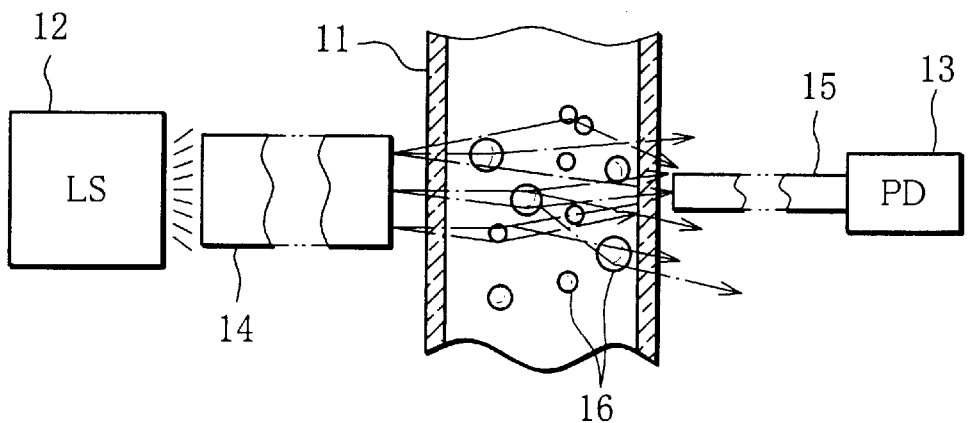
FIG. 3 is a diagram showing how bubbles produced in a tube are sensed in the ball detecting apparatus of FIG. 1.

In addition, in the present embodiment, the photo detector 13 is adapted such that when bubbles 16 are produced in the transparent liquid as shown in FIG. 3, the photo detector 13 receives, of the diffused light, a component that has been deflected by the bubbles 16 which act as concave lenses. Specifically, as mentioned above, the diffused light emitted from the surface light source 12 has a predetermined beam cross section and a predetermined beam spread angle. Based on this, even when the diffused light is deflected by the bubbles 16 and has its traveling direction changed, a component thereof enters the light receiving area of the photo detector 13 (optical fiber 15). Thus, the photo detector 13 receives the diffused light.

More specifically, even if a component of the diffused light that was traveling in the tube 11 straight toward the light receiving area of the photo detector 13 (optical fiber 15) is deflected by the bubbles 16 and deviates from the course to the light receiving area, another component of the diffused light that was originally taking a course that does not reach the light receiving area is deflected by the bubbles 16 and reaches the light receiving area. Thus, even when the component of the diffused light that was traveling straight toward the light receiving area (direct component) is all deflected by the bubbles 16 and does not reach the light receiving area, the photo detector 13 receives another component of the diffused light that was deflected by the bubbles 16 to enter the light receiving area (indirect component). The diffused light having a predetermined beam cross section and predetermined beam spread angle as mentioned above ensures that when a component of the diffused light is deflected by the bubbles 16 from its course to the light receiving area of the photo detector 13, another component thereof travels to the light receiving area of the photo detector 13. Thus, as shown in FIG. 3, even when the diffused light is deflected by the bubbles 16, the photo detector 13 surely receives part of the diffused light projected from the surface light source 12 to the tube 11.

Figure 4:
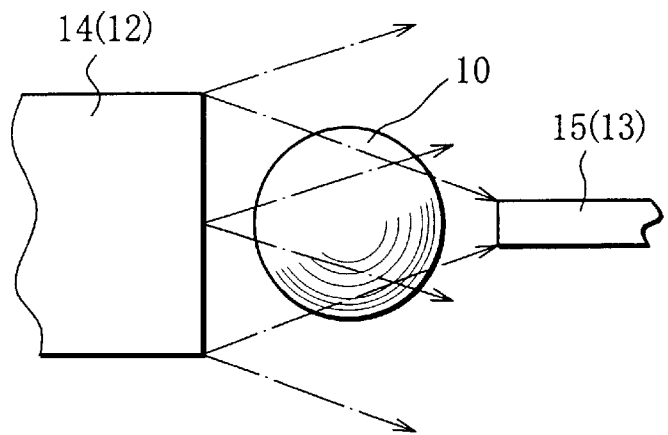
FIG. 4 is a diagram showing optical relation between a ball, a surface light source and a photo detector in the ball detecting apparatus of FIG. 1.

FIG. 4 schematically shows the optical relation between the ball 10, the surface light source 12 and the photo detector 13. A field of view of the photo detector 13 is determined by an angular aperture and the light receiving area of the photo detector 13. Therefore, as is understood from FIG. 4, by appropriately determining the dimensions of the surface light source 12, the dimensions of the light receiving area of the photo detector 13 and the optical location of the field of view taking account of the dimensions of the ball 10, the beam spread angle of the diffused light and the angular aperture of the photo detector 13, the optical system can be constructed such that the light receiving area of the photo detector 13 can be completely shielded from the diffused light by the ball 10 and that the photo detector 13 can surely receive part of the diffused light from the surface light source 12 when the ball 10 is not present. With the optical system constructed in that manner, balls 10 in the tube 11 can be surely detected without the bubbles 16 in the transparent liquid as a carrier affecting the detection.

Figure 5:
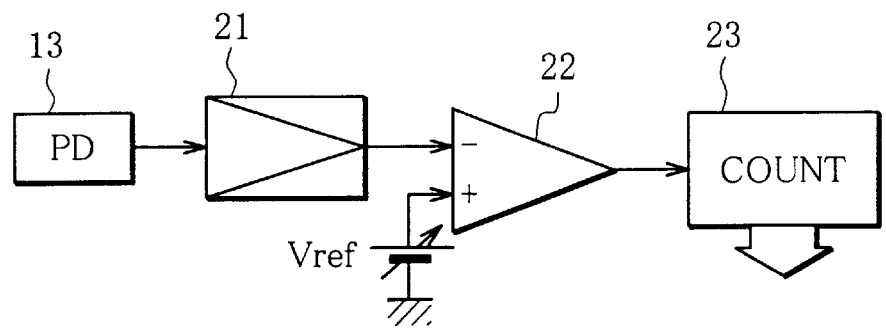
FIG. 5 is a diagram showing a structure of a judging circuit used in the ball detecting apparatus of FIG. 1.

A judging circuit for judging the presence of a ball 10 based on the output of the photo detector 13 (amount of received light) is structured, for example, as shown in FIG. 5. The judging circuit includes a pri-amplifier 21 for amplifying the output of the photo detector 13 to a predetermined level, and a comparator 22 for comparing the output of the pre-amplifier 21 and a predetermined reference value Vref. When the output of the pre-amplifier 21, which corresponds to the amount of light received by the photo detector, is at a level lower than the predetermined reference value Vref, the comparator 22 inverts the output of the pre-amplifier 21 to show that the ball 10 has been sensed. When the number of balls 10 carried in the tube 11 needs to be counted, it can be obtained by counting by a counter 23 how many times the output of the pre-amplifier 21 is inverted.

Figure 6:
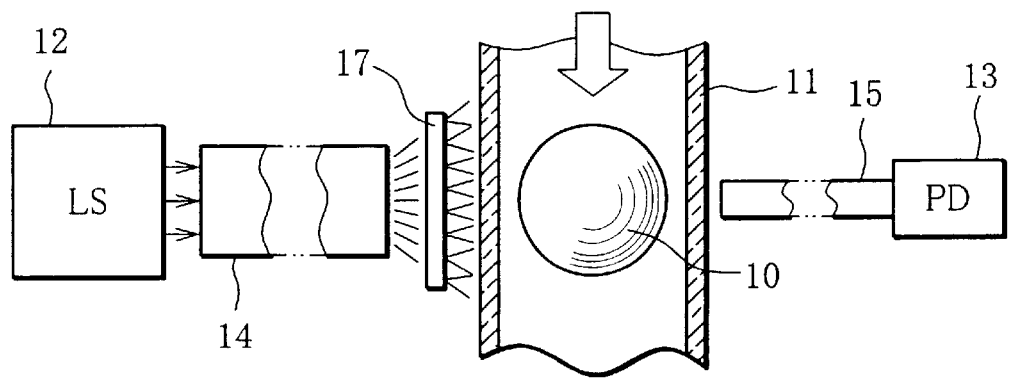
FIG. 6 is a diagram showing a schematic structure of a ball detecting apparatus according to another embodiment of the present invention.
Figure 7:
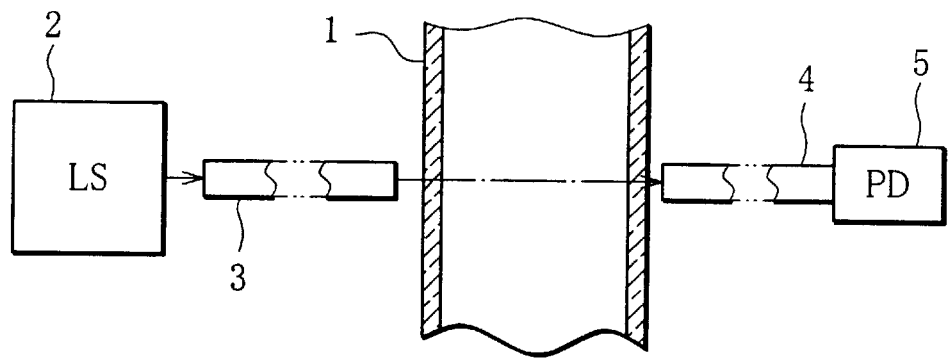
FIG. 7 is a diagram showing a structure and optical system of a conventional ball detecting apparatus.
Figure 8:
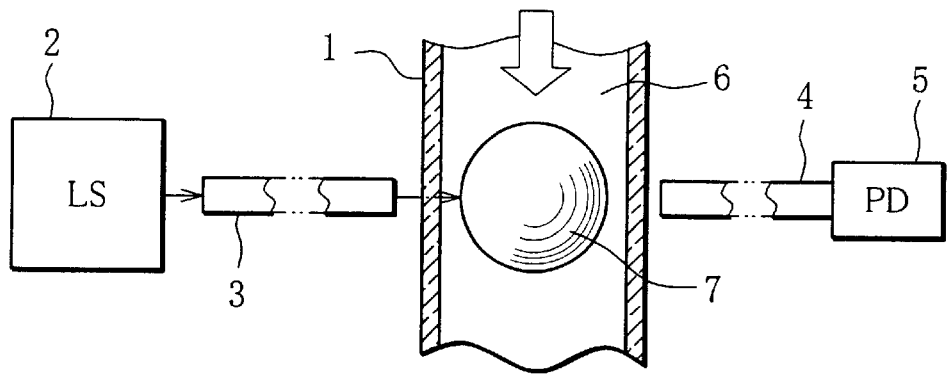
FIG. 8 is a diagram showing how a ball guided in a tube is sensed in the conventional ball detecting apparatus of FIG. 7.
Figure 9:
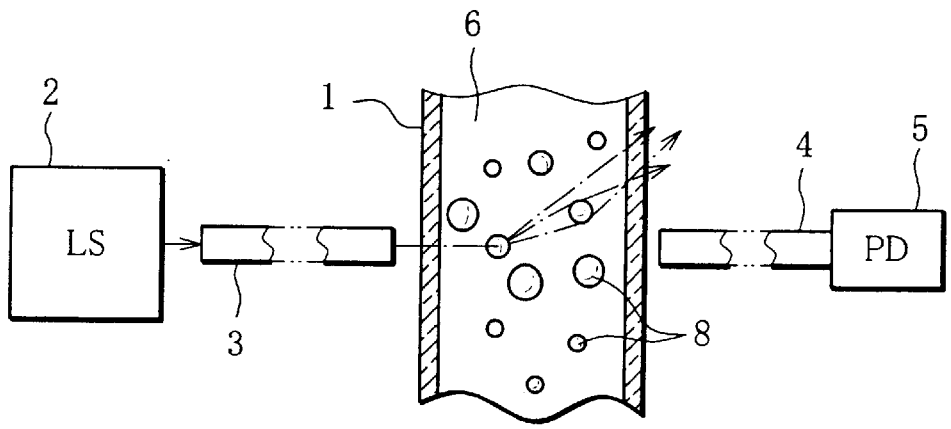
FIG. 9 is a diagram showing how bubbles produced in a tube are sensed in the conventional ball detecting apparatus of FIG. 7.

The present invention is not restricted to the above-described embodiment. In the above embodiment, the diffused light having a predetermined beam cross section and predetermined beam spread angle is projected to the tube 11 using the surface light source 12. However, such diffused light may be obtained by arranging a light diffusing plate 17 near the light projecting end of the optical fiber 14 for projection as shown in FIG. 6. In that case, for example, a semiconductor laser device that emits a laser beam having a predetermined beam diameter can be used for the light source. In the above embodiment, the light is guided using the optical fibers 13 and 14. However, the optical system may of course be so constructed that the diffused light emitted from the surface light source 12 directly enters the tube 11 and that the diffused light having crossed the tube 11 is directly received by the photo detector 13.

The beam cross section and beam spread angle of the diffused light, and the angular aperture, dimensions of light receiving area and optical location of field of view of the photo detector 13 may be determined depending on the dimensions of a to-be-detected ball 10 and the like. The present invention may undergo various other modifications not deviating from the spirit thereof.

What is claimed is:

1. A ball detecting apparatus for optically detecting non-transparent balls carried one by one by a transparent liquid through a transparent tube having an inner diameter slightly larger than a diameter of the balls, said ball detecting apparatus comprising:

a surface light source for projecting diffused light having a predetermined beam spread angle into said tube, a photo detector arranged opposite to said surface light source with said tube therebetween, and judging means for judging passage of said balls carried in said tube based on a light receiving signal produced by said photo detector, wherein said photo detector comprises a light receiving area for receiving both a component of the diffused light projected from said surface light source that has passed through said transparent liquid and a component of the diffused light projected from said surface light source that has been deflected by a bubble produced in said transparent liquid, wherein said light receiving area is adapted to be at least momentarily completely shielded from said diffused light by each of said balls as each of said balls passes through said tube, wherein said light receiving area of said photo detector is dimensioned such that a light receiving angle thereof can be completely covered by each of said balls at least momentarily as each of said balls passes through said tube, and wherein a light projecting area of said surface light source is greater than said light receiving area of said photo-detector.

2. A ball detecting apparatus for optically detecting non-transparent balls carried one by one by a transparent liquid through a transparent tube having an inner diameter slightly larger than a diameter of the balls, said ball detecting apparatus comprising:

a surface light source for projecting diffused light having a predetermined beam spread angle into said tube, a photo detector arranged opposite to said surface light source with said tube therebetween, and judging means for judging passage of said balls carried in said tube based on a light receiving signal produced by said photo detector, wherein said photo detector comprises a light receiving area for receiving both a component of the diffused light projected from said surface light source that has passed through said transparent liquid and a component of the diffused light projected from said surface light source that has been deflected by a bubble produced in said transparent liquid, wherein said light receiving area is adapted to be at least momentarily completely shielded from said diffused light by each of said balls as each of said balls passes through said tube, wherein said surface light source is arranged opposite to a first side of said tube with a first optical fiber therebetween, and said photo detector is arranged opposite to a second side of said tube with a second optical fiber therebetween, and wherein a diameter of said first optical fiber is greater than a diameter of said second optical fiber.

3. A ball detecting apparatus for optically detecting non-transparent balls carried one by one by a transparent liquid through a transparent tube having an inner diameter slightly larger than a diameter of the balls, said ball detecting apparatus comprising:

a surface light source for projecting diffused light having a predetermined beam spread angle into said tube, a photo detector arranged opposite to said surface light source with said tube therebetween, and judging means for judging passage of said balls carried in said tube based on a light receiving signal produced by said photo detector, wherein said photo detector comprises a light receiving area for receiving both a component of the diffused light projected from said surface light source that has passed through said transparent liquid and a component of the diffused light projected from said surface light source that has been deflected by a bubble produced in said transparent liquid, wherein said light receiving area is adapted to be at least momentarily completely shielded from said diffused light by each of said balls as each of said balls passes through said tube, and wherein said surface light source comprises a light diffusing plate.

4. A ball detecting apparatus according to claim 1, wherein said balls are ball-shaped semiconductor devices.

5. A ball detecting apparatus according to claim 2, wherein said balls are ball-shaped semiconductor devices.

6. A ball detecting apparatus according to claim 3, wherein said balls are ball-shaped semiconductor devices.

* * * * *